(12) United States Patent
Marknell Dewitt et al.

(10) Patent No.: US 7,279,295 B2
(45) Date of Patent: Oct. 9, 2007

(54) ALLERGEN

(75) Inventors: Asa Marknell Dewitt, Almunge (SE); Verena Niederberger, Vienna (AT); Pirjo Lehtonen, Uppsala (SE); Susanne Spitzauer, Vienna (AT); Wolfgang R. Sperr, Vienna (AT); Peter Valent, Vienna (AT); Rudolf Valenta, Vienna (AT); Jonas Lidholm, Knivsta (SE)

(73) Assignee: Phadia AB, Uppsala (SE)

( * ) Notice: Subject to any disclaimer, the term of this patent is extended or adjusted under 35 U.S.C. 154(b) by 0 days.

(21) Appl. No.: 10/400,071

(22) Filed: Mar. 27, 2003

(65) Prior Publication Data

US 2004/0014155 A1 Jan. 22, 2004

(30) Foreign Application Priority Data

Mar. 27, 2002 (SE) .................................. 0200946

(51) Int. Cl.
A61K 35/78 (2006.01)
A61K 39/35 (2006.01)
C07K 14/415 (2006.01)
G01N 33/536 (2006.01)
G01N 33/543 (2006.01)

(52) U.S. Cl. ................ 435/7.91; 424/184.1; 424/185.1; 424/275.1; 424/276.1; 435/7.1; 435/7.95; 435/69.3; 435/975; 436/518; 436/536; 436/543; 530/370

(58) Field of Classification Search ............. 424/275.1, 424/184.1, 185.1, 257.1; 435/7.1, 7.91, 7.95, 435/64.3, 975; 436/518, 536, 543; 530/370
See application file for complete search history.

(56) References Cited

FOREIGN PATENT DOCUMENTS

WO 03/047618 * 6/2003

OTHER PUBLICATIONS

D'Amato, G. et al.; "Position paper, Pollen-related allergy in Europe"; *ALLERGY*; Munksgaard 1998,53, pp. 567-578.
Esch, Robert E.; "Grass Pollen Allergens"; *Allergen and Allergen Immunotherapy, Second Edition, Revised and Expanded*; Marcel Dekker, Inc., New York, 1999, pp. 103-120.
Laffer, Sylvia et al.; "Complementary DNA cloning of the major allergen Phl p I from timothy grass (*Phleum pratense*); recombinant Phl p I inhibits IgE binding to group I allergens from eight different grass species"; *J Allergy Clin Immunol*, Oct. 1994, 94, 4, pp. 689-698.
Petersen, Arnd et al.; "Structural investigations of the major allergen Phl p I on the complementary DNA and protein level"; *J Allergy Clin Immunol*, May 1995, 95, 5, 1, pp. 987-994.
Dolecek, Christiane et al.; "Molecular characterization of Phl p II, a major timothy grass (*Phleum pratense*) pollen allergen"; *FEBS Letters*; Dec. 1993, 35, 3, pp. 299-304.

Vrtala, Susanne et al.; "cDNA Cloning of a Major Allergen from Timothy Grass (*Phleum pratense*) Pollen; Characterization of the Recombinant Phl p V Allergen"; *The Journal of Immunology*; Nov. 1993, 151, 9, pp. 4773-4781.
Bufe, Albrecht et al.; "Major allergen Phl p Va (timothy grass) bears at least two different IigE-reactive epitopes"; *J Allergy Clin Immunol*; Aug. 1994, 94, 2, pp. 173-181.
Bufe, A. et al.; "Major allergen Phl p Vb in timothy grass is a novel pollen Rnase"; *FEBS Letters 363*; 1995, pp. 6-12.
Petersen, A. et al.; "Characterization of the Allergen Group VI in Timothy Grass Pollen (Phl p 6); cDNA Cloning of Phl p 6 and Structural Comparison to Grass gGroup V"; *Int Arch Allergy Immunol*; 1995, 108, pp. 55-59.
Vrtala, Susanne et al.; "Molecular, Immunological, and Structural Characterization of Phl p 6, a Major Allergen and P-Particle-Associated Protein from Timothy Grass (*Phleum pratense*) Pollen"; *Characterization of a Major Timothy Grass Pollen Allergen, Phl p 6*; 1999, pp. 5489-5496.
Niederberger, Verena et al.; "Calcium-dependent immunoglobulin E recognition of the apo- and calcium—bound form of a cross-reactive two EF-hand timothy grass pollen allergen, Phl p 7"; *The FASEB Journal*; May 1999, 13, pp. 843-856.
Valenta, Rudolf et al.; "cDNA cloning and expression of timothy grass (*Phleum pratense*) pollen profiling in *Escherichia coli*: comparison with birch pollen prolifin"; *Biological and Biophysical Research Communications*; Feb. 1994, 199, 1, pp. 106-117.
Suck, R. et al.; "Complementary DNA cloning and expression of a newly recognized high molecular mass allergen Phl p 13 from timothy grass pollen (*Phleum pratense*)";*Clinical and Experimental Allergy*; 2000, 30, pp. 324-332.
Niederberger, Verena et al.; "IgE antibodies to recombinant pollen allergens (Phl p1, Phl p 2, Phl p 5 and Bet v 2) account for a high percentage of grass pollen-specific IgE"; *J Allergy Clin Immunol*; 1998, 101, pp. 258-264.
Valenta, Rudolf et al.; "Identification of Profilin as a Novel Pollen Allergen; IgE Autoreactivity in Sensitized Individuals"; *Science*; 253, pp. 557-560.
Valenta, Rudolf et al.; "Prolifins Constitute a Novel Family of Functional Plant Pan-allergens", *J. Exp. Med.*; Feb. 1992, 175, pp. 377-385, 1991.
Ball, Tanja et al.; "Induction of antibody responses to new B cell epitopes indicates vaccination character of allergen immunotherapy"; *Eur. J. Immunol*; 1999, 29, pp. 2026-2036.
Chirgwin, John M. et al.; "Isolation of Biologically Active Ribonucleic Acid from Sources Enriched in Ribonuclease"; *Isolation of RNA with Guanidinum Thocyanate*; 1979, 18, 24, pp. 5294-5299.
Innis, M. A. et al.; "Rapid Amplification of Complementary DNA Ends for Generation of Full-Length Complementary DNAs: Thermal RACE"; *PCR for Amplifying and Manipulating DNA*; 1993, 218, pp. 340-356.
Crosa, Jorge H. et al.; "Construction and Characterization of New Cloning Vehicles; A Multipurpose Cloning System"; *GENE*; 1977, 2, pp. 95-113.

(Continued)

*Primary Examiner*—Long V. Le
*Assistant Examiner*—James L. Grun
(74) *Attorney, Agent, or Firm*—Browdy and Neimark, PLLC

(57) ABSTRACT

The present invention relates to a novel allergen from timothy grass (*Phleum pretense*) pollen, Phl p11 as disclosed in SEQ ID NO:2, and use thereof as a reagent and in a diagnositic kit as well as for immunotherapy.

7 Claims, 5 Drawing Sheets

OTHER PUBLICATIONS

Figure 1:
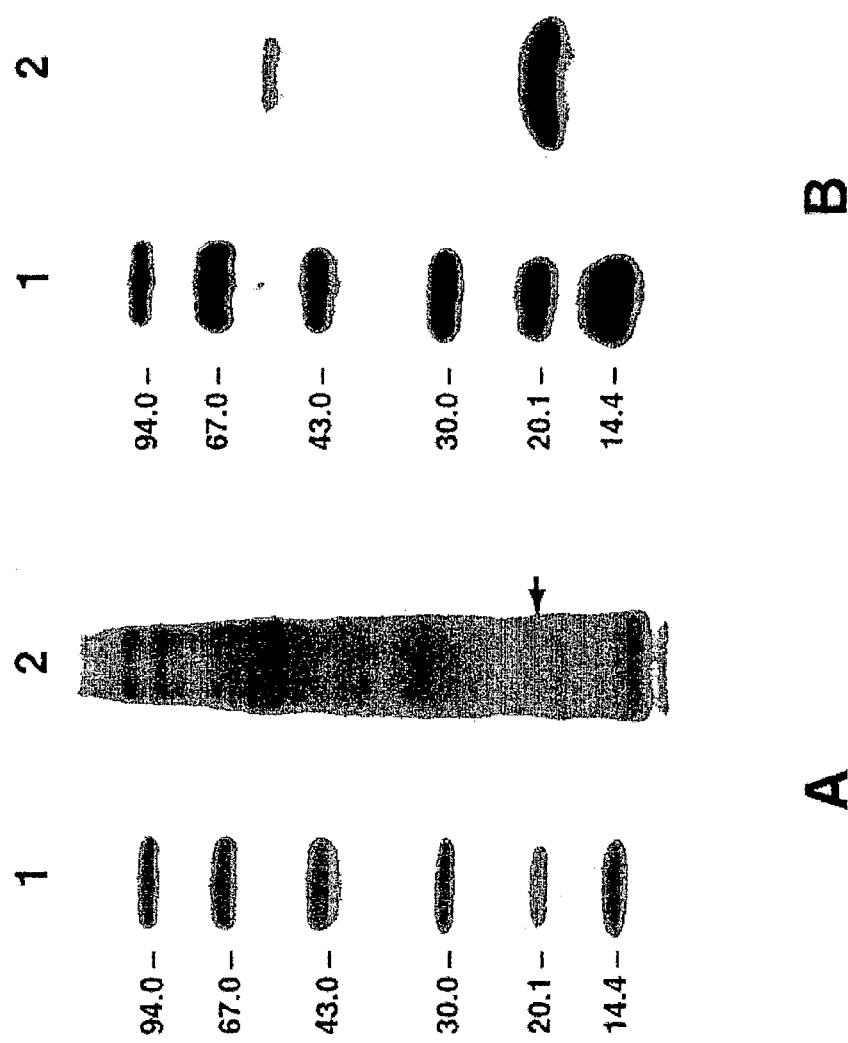

Valent, P. et al.; "Interleukin 3 activates human blood basophils via high-affinity binding sites"; *Proc. Natl. Acad. Sci.*; Jul. 1989, 86, pp. 5542-5546.

Valenta, Rudolf et al.; "Induction of specific histamine release from basophils with purified natural and recombinant birch pollen allergens"; *J Allergy Clin Immunol*; 91, 1, pp. 88-97, 1993.

Vrtala, Susanne et al.; "Conversion of the Major Birch Pollen Allergen, Bet v 1, into Two Nonanaphylactic T Cell Epitope-containing Fragments, Candidates for a Novel Form of Specific Immunotherapy"; *Recombinant Nonanaphylactic Bet v 1 Fragments for Immunotherapy*; Apr. 1997, 99, 7, pp. 1673-1681.

Van Ree, Ronald et al.; "Lol p XI, a new major grass pollen allergen, is a member of a family of soybean trypsin inhibitor-related proteins"; *J Allergy Clin Immunol*; 1995, 95, 5, pp. 970-978.

Calabozo, B. et al.; "Structural and Antigenic Similarity Between PLA L 1 and Ole E 1, the major Allergens of English Plantain and Olive Pollens", *The Journal of Allergy and Clinical Immunology*; Feb. 2001, 107, 2, p. S15.

Valenta, R. et al.; "The recombinant allergen-based concept of component-resolved diagnostics and immunotherapy (CRD and CRIT)"; *Clinical and Experimental Allergy*; 1999, 29, pp. 896-904.

Mertens, Nico et al.; "Tight Transcriptional Control Mechanism Ensures Stable High-Level Expression from T7 Promoter-Based Expression Plasmids"; *Bio/Technology*; Feb. 1995, 13, pp. 175-179.

Van Der Veen, Maurita J. et al.; "Allergens, IgE, mediators, inflammatory mechanisms, Poor biologic activity of cross-reactive IgE directed to carbohydrate determinants of glycoproteins"; *J Allergy Clin Immunol*; Sept. 1997, 100, 3, pp. 327-334.

Aalberse, R. C. et al.; "Crossreactive Carbohydrate Determinants"; *Clinical Reviews in Allergy and Immunology*; 1997, 15, pp. 375-387.

Aalberse, R.C.; "Clinical relevance of carbohydrate allergen epitopes"; *Allergen*; 1998, 53, pp. 54-57.

Mari, Adriano et al.; "Specific IgE to cross-reactive carbohydrate determinants strongly affect the in vitro diagnosis of allergic diseases"; *J Allergy Clin Immunol*; Jun. 1999, 103, pp. 1005-1011.

Van Ree, Ronald et al.; "Specific IgE without clinical allergy"; *J Allergy Clin Immunol*; 103, 6, pp. 1000-1001, 1999.

Barderas, Rodrigo et al.; "Isolation and Cloning of Che a 1, Allergen From Chenopodium Album Pollen"; *J Alergy Clin Immunol*;; 107, 2, p. S19, 2001.

* cited by examiner

Fig. 2

| | | | | | | | | | | | | | | |
|---|---|---|---|---|---|---|---|---|---|---|---|---|---|---|
| Asp | Lys | Gly | Pro | Gly | Phe | Val | Val | Thr | Gly | Arg | Val | Tyr | Cys | Asp | 15
| GAC | AAG | GGC | CCG | GGC | TTC | GTG | GTC | ACG | GGA | CGC | GTC | TAC | TGC | GAC | 45

```
Asp Lys Gly Pro Gly Phe Val Val Thr Gly Arg Val Tyr Cys Asp    15
GAC AAG GGC CCG GGC TTC GTG GTC ACG GGA CGC GTC TAC TGC GAC    45

Pro Cys Arg Ala Gly Phe Glu Thr Asn Val Ser His Asn Val Gln    30
CCC TGC CGC GCC GGC TTC GAG ACC AAC GTC TCC CAC AAC GTC CAA    90

Gly Ala Thr Val Ala Val Asp Cys Arg Pro Phe Asn Gly Gly Glu    45
GGG GCG ACC GTG GCG GTG GAC TGC CGG CCG TTC AAC GGC GGC GAG    135

Ser Lys Leu Lys Ala Glu Ala Thr Thr Asp Gly Leu Gly Trp Tyr    60
AGC AAG CTC AAG GCG GAG GCG ACG ACG GAC GGT CTG GGC TGG TAC    180

Lys Ile Glu Ile Asp Gln Asp His Gln Glu Glu Ile Cys Glu Val    75
AAG ATC GAG ATC GAC CAG GAC CAC CAG GAG GAG ATC TGC GAG GTG    225

Val Leu Ala Lys Ser Pro Asp Thr Thr Cys Ser Glu Ile Glu Glu    90
GTG CTG GCC AAG AGC CCC GAC ACG ACG TGC TCC GAG ATC GAG GAG    270

Phe Arg Asp Arg Ala Arg Val Pro Leu Thr Ser Asn Asn Gly Ile    105
TTC CGC GAC CGC GCC CGC GTC CCG CTC ACC AGC AAC AAC GGC ATC    315

Lys Gln Gln Gly Ile Arg Tyr Ala Asn Pro Ile Ala Phe Phe Arg    120
AAG CAG CAG GGC ATC CGC TAC GCC AAC CCC ATC GCA TTC TTC CGC    360

Lys Glu Pro Leu Lys Glu Cys Gly Gly Ile Leu Gln Ala Tyr Asp    135
AAG GAG CCG CTC AAG GAG TGC GGC GGC ATC CTC CAG GCC TAC GAC    405

Leu Arg Asp Ala Pro Glu Thr Pro *                              143
CTC AGG GAC GCC CCC GAG ACG CCA TGA AGC CCC ACA CCA GCA CGA    450

CGT ACC ACC TAT AGT TAC TTG CCG CCG GCC GAG ACG ATG TTA CCT    495
                               ▽
CTG CGA GCC GCT GCC GGA GAG GAR ATG ACA ACC TTT TAA TGG GCC    540
                        ▽
TCA CGT GCG CCT TAA TAT TCR CGT CCT GCT TTC TCT TTT ATT CAT    585
                ▽
GTT ATT GTC TTC CTG TYC TCT AAT TAT TTA CGT GTT GAC CTA TAT    630
                                                  ▼
GTG AGC TAG TTC CAA GGA TCT GTT CTA TGT GTA ATA AGA GAA CAC    675
        ▽    ▼                                          ▽
AAA TAT TTS GTA CGT GCA TAT CCG ATG TAT ATC CTC TTT TCG GGG    720
        ▽▽   ▽                                       ▽
AAA AAA AAW AYT CTG ATG TAT ATC CTC TGG ACA CAA ATT AAR TGG    765
        ▼       ▽ ▼
CCA GCT AAT GAA TTS AGT ACT (A)n                               803+
 ▽
```

Fig. 3

```
ruler     1                                                          60
Phl p11                                  DK--GPGFVVTGRVYCDPCRAGFETNVSHNVQG
A54002                                   DK--GPGFVVTGRVYCDPCRAGFETNVSHNVEG
1815759   MASLR--ALSVIAVAVVLFALADTAVATK--APDYVVQGRVYCDRCRAGFETNVTEYIKG
S31710    MASLR--TIPVIFG-ILFYVLASTATATD--APDYVVQGRVYCDTCRAEFETNVTEYIKG
P33050    MASVPAPATTTAAVILCLCVVLSCAAADDPNLPDYVIQGRVYCDTCRAGFVTNVTEYIAG
2765366        MAKSIIIQAP-ALCFLSLLGFAYSES----RFFVEGKVYCDNCRTQFVTKLSTYMKG
P13447         MAKAIVLLSA---LCIIALANFAHCRP---EVFDVEGKVYCDTCRVQFETKLSENLEG
2832664       MASKAIFFFFVSAVCLSSLAGVAIADADDFDRFQIQGSVYCDTCRVQFVTRLSKFLEG
398899                               ARPNK---NPFVXRGRVYCDTCXVXFETPASTYISG
S43242                               EDVPQPPI---PQFHIQGQVYCDTCRARFITELSEFIPG
S43244                               EDVPQPPV---PQFHIQGQVYCDTCRARFITELSEFIPG
3256212                              EDVPQPPV---SQFYIQGQVYCDTCRARFITELSEFIPG
926885                               EDVPQPPV---SQFYIQGQVYCDTCRAGFITELSEFIPG ruler     61                                                         120
Phl p11   ATVAVDCRPFNGGESKLKAEATTDGLGWYKIEIDQDHQEEICEVVLAKSPDTTCSEIEEF
A54002    ATVAVDCRPFDGGESKLKAEATTDKDGWYKIEIDQDHQEEICEVVLAKSPDKSCSEIEEF
1815759   AKVRLECRHFGTNVLERAIDGVTDETGTYKIELRDSHVEDICEVVLVKSPLADCHEIQSL
S31710    AKVRLECKHFGTDKVERAIDGVTDETGTYKIELKDSHEEDICEVVLVHSPLANCSEIEAE
P33050    AKVRLECKHFGTGKLERAIDGVTDATGTYTIELKDSHEEDICQVVLVASPRKDCDEVQAL
2765366   AKVSLECRNREGGTLIYSSDSETDKSGTYRIPVDGDHEEEICEIALKKSSDPDCSEVSKD
P13447    ATVKLQCRNISTEAETFSVEGVTDKDGKYKLTVNGDHENDICEVTVVKSPREDCKESVSG
2832664   .AKVKLECRSRTNGTVTLTKEAVTDKTGSYRMEVTGDHEEEVCELVLVESPDSGCSDVSKE
398899    AVVRLECKDRRTMELTYSHEARTDSTGSYKILVNEDHDEQFCDAMLVRSSQLRCSNVSPG
S43242    ASIRLQCKDRENGKITFTEIGYTRAEGLYSMLVEGDHKNEFCEITLISSGREDCDEIPVE
S43244    ASIRLQCKDGENGKITFTEIGYTRAEGLYSMLVEGDHKNEFCEITLISSGRKDCDEIPVE
3256212   AGVRLQCKDGENGKITFTEVGYTRAEGLYSMLIERDHKNEFCEITLLSSSRKDCDEIPIE
926885    ASVRLQCKEKKNGDITFTEVGYTRAEGLYSMLVERDHKNEFCEITLISSGSKDCNEIPTE ruler     121                                                        175
Phl p11   ---RDRARVPLTSNNGIKQQGIRYANPIAFFRKEPLKECGGILQAYDLRDAPETP
A54002    ---RDRARVPLTSNXGIKQQGIRYANPIAFFRKEPLKECGGILQAY
1815759   ---RDRAPVLLTRNVGISDN-LRLANPLGYLKDVPLPVCGDLLKMFKLADDDDDQ
S31710    ---RDRARVLLTRNVGICDN-LRLANPLGYLKDYHCPS-AALLKQFDLADDDDNE
P33050    ---RDRAGVLLTRNVGISDS-LRPANPLGYFKDVPLPVCAALLKQLDSDDDDDQ
2765366   PFLKKSARISLTKNNGIS-TPVRLANPLGFMKKKPLPECAKALRELGMNPDDVIQ
P13447    ---YEKARIECSDNVGI-HNAVRFANPLFFMKAESVQGCKEALDELGLFPLEF
2832664   AYLRNAAKISLTANDGIVSHETRIVNPLGFMVQTPSAECPAAFKELGIVPDG
398899    ---HDRARVTLTRFNGIASD-DRFANNMGFLRDAAMPGCADIMKLYQETE
S43242    GWAKPSLKFKLNTVNG----TTRTINPIGFFKKEALPKCTQVYNKLGMYPPNM
S43244    GWVKPSLKFKLNTVNG----TTRTINPIGFFKKEALPKCTQVYNKLGMYPPNM
3256212   GWVKPSLKFMLNTVNG----TTRTINPLGFFKKEALPKCPQVFNKLGMYPPNM
926885    GWAKPSLKFILNTVNG----TTRTVNPLGFFKKEALPKCAQVYNKLGMYPPNM
```

ALLERGEN

FIELD OF THE INVENTION

The present invention relates to a novel allergen from timothy grass (*Phleum pratense*) pollen, Phl p 11, and use thereof as a reagent and in a diagnostic kit as well as for immunotherapy.

BACKGROUND OF THE INVENTION

A hallmark of atopic allergy is the formation of IgE antibodies to proteins present in the sensitizing biological material. Upon contact with the allergen source, these proteins will act to crosslink IgE antibodies present on the surface of mast cells, thereby eliciting the release of inflammation mediators such as histamine. As a result, an allergic reaction occurs (1).

In the industrialized world, up to 10% of the human population shows allergic sensitization to grass pollen, making this one of the most important airborne allergen sources (2). Considerable efforts have been made towards the characterization of pollen allergens from a variety of grass species using biochemical and immunological methods. A number of IgE binding proteins have thus been identified which exhibit conserved structure and serological cross-reactivity between species. Based on these criteria, such immunologically related grass pollen allergens have been assigned to groups designated by numbers. These include group 1, group 2/3, group 4, and group 5 allergens, which are represented in pollen of most grass species (3).

To date, six different allergens from timothy grass (*Phleum pratense*) pollen have been cloned: Phl p 1 (4, 5), Phl p 2 (6), Phl p 5 (7-9), Phl p 6 (10, 11), Phl p 7 (12), Phl p 12 (profilin) (13), and Phl p 13 (14). These allergens have all been produced as recombinant proteins which, by different in vitro and in vivo activity assays, have been shown to share immunological and allergenic properties with their native counterparts.

Using a panel of four recombinant allergens (rPhl p 1, rPhl p 2, rPhl p 5, and profilin) in serological and skin testing procedures, positive results were obtained in 95% of a large population of grass pollen-allergic individuals (15). Sensitization to allergens such as Phl p 7 (a calcium-binding, two-EF-hand protein) and Phl p 12 occurs in a smaller proportion of grass pollen allergics, but they share IgE epitopes with homologous proteins present in pollen of trees and weeds and can therefore cause immediate-type symptoms in sensitized individuals upon contact with these unrelated allergen sources (12, 16, 17).

SUMMARY OF THE INVENTION

The present invention relates to a novel allergen from timothy grass (*Phleum pratense*) pollen, Phl p11. While the absolute majority of grass pollen allergics produce IgE antibodies binding to group 1 and group 5 grass pollen allergens—Phl p 1 and Phl p 5 in the case of timothy grass pollen, a subset of the patients also make IgE antibodies to a variety of other protein components such as profilin, Phl p 7 or Phl p 11. These patients are thought to have a more expansive immunological activity in their allergic disease, putting them at greater risk of developing clinical reactivity to an increasing number of allergen sources (such as weed and tree pollens, cat and dog dander, mites, etc).

Profilin and Phl p 7 are highly cross-reactive (vegetables, fruits and pollens of weeds and trees) and not specifically indicative of sensitisation to the grass pollen proteins. Antibody binding structures present on Phl p 11, on the other hand, appear to be specific to grass pollen and may therefore be regarded as a marker of multivalent sensitisation to this particular allergen source, i.e. a marker of enhanced overall propensity to produce IgE antibodies to environmental substances. Recombinant Phl p 11 may be used to identify the subset of patients which are sensitized to polypeptide structures of Phl p 11 and its homologues in pollen of other grass species. About half of all patients that show IgE reactivity to this pollen protein reportedly have their antibodies directed to glycan structures present on the group 11 allergen. These glycan structures are cross-reactive in nature and antibodies binding to them may not be informative/diagnostic in relation to grass pollen-specific sensitisation. IgE reactivity to rPhl p 11 may thus be informative with respect to state of immunological diversification of patients' allergic sensitisation to grass pollen, independent of other allergen sources.

As a defined immunotherapy reagent, recombinant Phl p 11 may be used to treat specifically sensitised patients by way of eliciting a protective or attentuating immune response. The active substance may be a protein comprised of either the natural ("wild-type") polypeptide sequence or a derivative with improved safety or efficacy properties.

Thus, in a first aspect the invention relates to a reagent which may be recombinantly produced or chemically synthesized, Phl p11, comprising the amino aid sequence according to SEQ ID NO 1 of the enclosed sequence listing as well as essentially homologous (such as 75%) and cross-reactive variants and derivatives thereof. These variants have equivalent or similar function with respect to antibody binding. The invention also relates to DNA sequences encoding said amino acid sequence.

In a second aspect, the invention relates to a diagnostic kit comprising the above reagent. The diagnostic kit may also comprise one or more other known Phl allergens, such as Phl p 1, Phl p 2, Phl p 4, Phl p 5a, Phl p 5b, Phl p 6, Phl p 7, Phl p 12 and Phl p 13.

In a third aspect, the invention relates to an immunoassay comprising the following steps:
a) obtaining a patient blood sample from a patient with suspected grass pollen allergy
b) allowing serum or plasma derived from the blood sample to contact the allergen reagent, immobilized on a solid phase or in solution.
c) detecting antibodies bound to the allergen reagent using a specific detection reagent such as an enzyme-conjugated anti-IgE antibody.

The immunoassay may comprise the reagent Phl p 11, either natural or recombinantly produced or chemically synthesized. The immunoassay may be in any desired format, such as ELISA.

In a fourth aspect, the invention relates to use of the above reagent or a derivative thereof for production of a drug for immunotherapy ("allergy vaccination") of grass pollen allergic patients showing IgE antibody reactivity to Phl p 11. Preferably, the use is for immunotherapy ("allergy vaccination") of timothy grass pollen allergic patients showing IgE antibody reactivity to Phl p 11.

DETAILED DESCRIPTION OF THE INVENTION

Figure Legends

FIG. 1. Identification of Phl p 11 using SDS-PAGE and immunoblot analysis of *P. pratense* pollen extract. A: Pollen extract was reduced and separated by SDS-PAGE, followed by staining with Coomassie Brilliant Blue. The faint protein band identified as Phl p 11 is marked with an arrow. B: Immunoblot analysis of a duplicate gel, where the binding of one patient's serum IgE antibodies is visualized. Lane 1: molecular weight markers, lane 2: *P. pratense* pollen extract.

FIG. 2. Nucleotide (SEQ ID NO:1) and deduced amino acid sequence (SEQ ID NO:2) of Phl p 11 cDNA. An open reading frame identical to all clones conformed closely with the codon preference derived from all published *P. pratense* genes expressed in pollen. The underlined nucleotide sequences represent primers GSP-1 (SEQ ID NO:15) and GSP-2 (SEQ ID NO:20). Open arrowheads indicate nucleotide differences between the clones that were analyzed; the standard nucleotide ambiguity codes are used at those positions. Homopolymer stretch length variation between the clones is indicated by shading. The sequence shown represents the longest of five analyzed clones, while black arrowheads mark where the other cDNAs ended in a poly-A stretch. The amino acid sequence marked by solid underlining represents the 20 residues which were determined by N-terminal microsequencing of the natural pollen protein. A single site for potential N-linked glycosylation is indicated by dotted underlining.

FIG. 3. Multiple amino acid sequence alignment of Phl p 11 (SEQ ID NO:2) and structurally related proteins. Each sequence retrieved from the database is preceded by its accession number: A54002 (*Lolium perenne*; SEQ ID NO:3), 1815759 (*Phalaris coerulescens*; SEQ ID NO:4), S31710 (*Oryza sativa*; SEQ ID NO:5), P33050 (*Zea mays*; SEQ ID NO:6), 2765366 (*Betula pendula*; SEQ ID NO:7), P13447 (*Lycopersicon esculentum*; SEQ ID NO:8), 2832664 (SEQ ID NO:9) and 398899 (*Arabidopsis thaliana*; SEQ ID NO:10), S43242 (SEQ ID NO:11) and S43244 (*Syringa vulgaris*; SEQ ID NO:12), 3256212 (*Ligustrum vulgare*; SEQ ID NO:13), and 926885 (*Olea europaea*; SEQ ID NO:14). All entries are shown in full, except the *A. thaliana* sequence 2832664 (SEQ ID NO:15) which was truncated to show only the domain aligning with the protein family examined here. Positions marked x indicate unidentified or atypical residues. The third through eighth sequence include a putative N-terminal leader peptide. Hyphens indicate gaps introduced to maximize the number of aligning residues.

Figure 4:
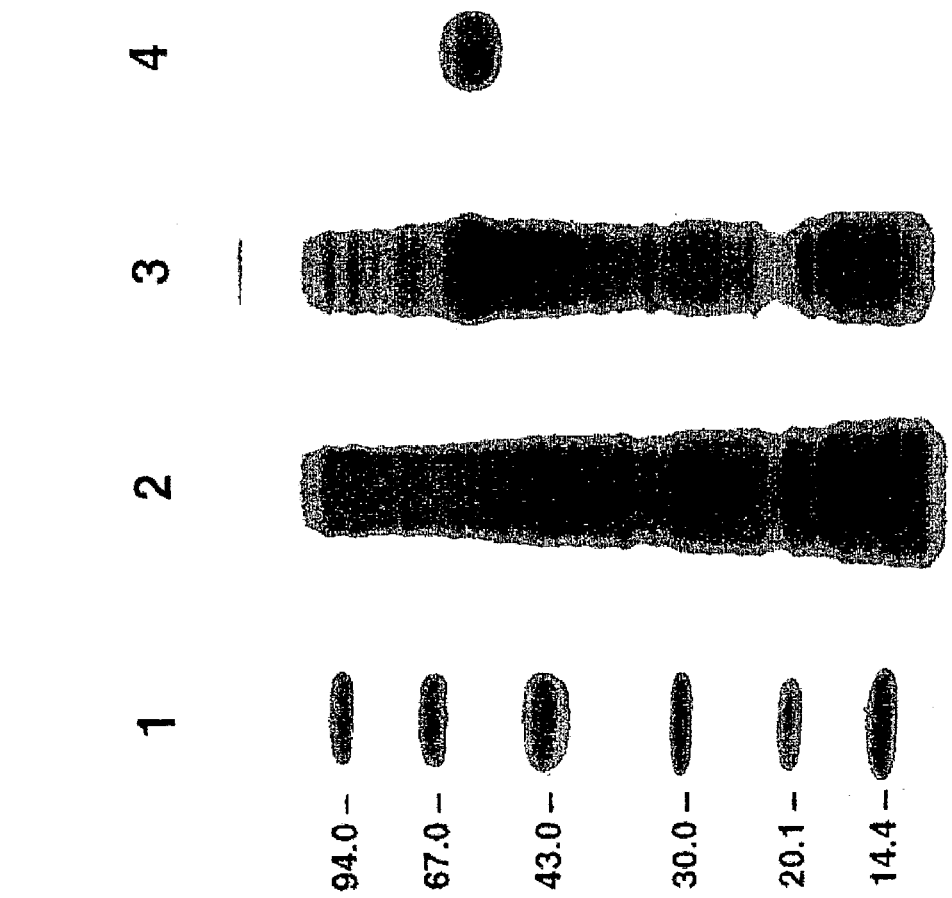

FIG. 4. Analysis of recombinant Phl p 11 expression in *E. coli*. An *E. coli* strain prepared for expression of a MBP-Phl p 11 fusion protein was grown to mid log phase and then subjected to a temperature shift in order to de-repress the expression system. Samples were prepared by boiling pelleted cells in loading buffer containing SDS and β-mercaptoethanol. Lane 1: molecular weight markers, lane 2: pre-induction sample, lane 3: postinduction harvest, lane 4: sample of purified protein. Proteins were visualized by Coomassie Brilliant Blue staining.

Figure 5:
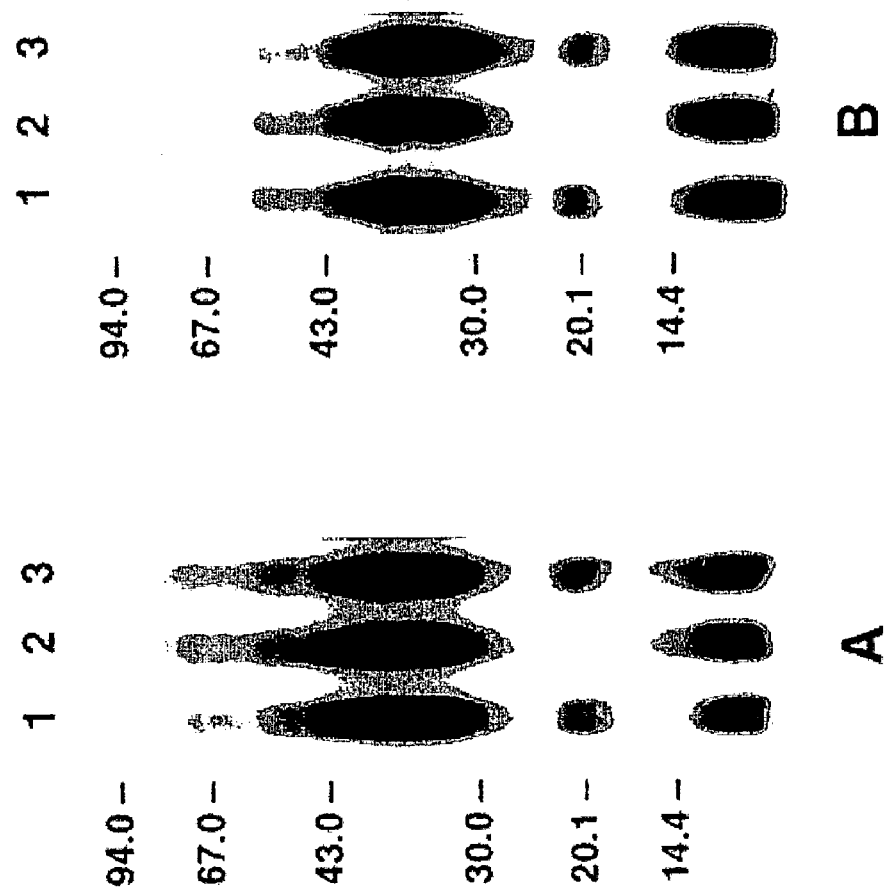

FIG. 5. Immunoblot inhibition of IgE binding to immobilized *P. pratense* extract proteins by soluble rPhl p 11. Pollen extract was reduced and separated by SDS-PAGE, and electroblotted onto nitrocellulose membrane. The membrane was incubated with serum samples from two Phl p 11-sensitized grass pollen-allergic subjects (A and B), after preincubation with either BSA (lane 1), rPhl p 11 (lane 2) or MBP (lane 3).

MATERIALS AND METHODS

General Reagents, Plasmids, Oligonucleotides, Bacterial Strains and Antibodies

Salts and buffers were purchased from Sigma (St. Louis, Mo.) and Fluka (Buchs, Switzerland). Pollen from timothy grass (*Phleum pratense*) was obtained from Pharmacia Allergon AB (Välinge, Sweden). Protein analysis by SDS-PAGE was performed using 4-20% Tris-glycine gels (Novex, San Diego, Calif.) and for electroblotting Hybond-C Extra membrane (Amersham Life Science, Amersham, UK) was used. For immunoblot analysis of IgE binding, rabbit anti-IgE antiserum (MLAB, Uppsala, Sweden) and horseradish peroxidase-conjugated donkey anti-rabbit IgG (Amersham Life Science) were used, followed by ECL detection (Amersham Life Science). Preparation of polyadenylated RNA from total RNA and subsequent synthesis of cDNA for RT-PCR were performed using the mRNA Purification Kit and the First-strand cDNA Synthesis Kit, both from Amersham Pharmacia Biotech (Uppsala, Sweden). Plasmids pET-23a(+) and pMAL-c2 were purchased from Novagen (Madison, Wis.) and New England Biolabs (Beverly, Mass.), respectively. Restriction endonucleases EcoRI, HindIII, NdeI and XhoI, as well as Taq DNA polymerase and deoxynucleotides were from Amersham Pharmacia Biotech. Pfu DNA polymerase was purchased from Stratagene (La Jolla, Calif.). DNA from PCR and other enzyme reactions was purified using appropriate Wizard kits from Promega (Madison, Wis.). For solid phase capture of biotinylated PCR products, streptavidin-modified magnetic beads (M-280) from Dynal AS (Skøyen, Norway) were used. For large-scale plasmid preparation, the Plasmid Maxi Kit from Qiagen (Düsseldorf, Germany) was used. Oligonucleotides were obtained from Scandinavian Gene Synthesis (Köping, Sweden). DNA sequencing was performed using the T7 Sequencing Kit from Amersham Pharmacia Biotech and [α-$^{35}$S]dATP from Amersham Life Science. The *E. coli* strains used were XL1-Blue MR (Stratagene) for cloning purposes and BL21 (Novagen) harboring plasmid pT7POL23 (18) for expression. HiTrap Chelating columns (Amersham Pharmacia Biotech) were used for immobilized metal ion affinity chromatography (IMAC). Buffer exchange and size exclusion chromatography of protein preparations were performed using an FPLC system and columns packed with Sephadex G-25 and Superdex 75, respectively (Amersham Pharmacia Biotech). Quantitative serology for the recombinant allergen was established using Pharmacia CAP System (Pharmacia Diagnostics), employing reagents and procedures as recommended by the supplier. For IgE detection in immunoblot inhibition experiments, an $^{125}$I-labeled anti-human IgE antibody from Pharmacia Diagnostics was used. Histamine release from isolated granulocytes of allergic and healthy individuals was measured by a radioimmunoassay (Immunotech, Marseille, France). As a positive control for histamine release capacity of cells, the monoclonal anti-IgE antibody E124.2.8 Dε2 (Immunotech) was used. Histamine and sodium chloride solution for skin prick tests were obtained from ALK (Hørsholm, Denmark).

Patient Samples

A total of 188 grass pollen-allergic subjects or serum samples were examined in this study. One hundred and fifty serum samples were from an in-house collection at Pharmacia Diagnostics, selected on the basis of IgE sensitization to *P. pratense*. Thirty-eight subjects were from a Vienna clinic and were characterized by case history indicative of grass pollen allergy, positive RAST result for timothy grass pollen, and positive skin prick test to grass pollen extract. The allergen sensitization profiles of these subjects were established with natural and recombinant timothy grass pollen allergens as described (19). Serum samples from two non-allergic individuals were included for control purposes.

Protein Extracts, SDS-PAGE and Immunoblot Analysis

*Phleum pratense* pollen was extracted at room temperature for 2 hrs in 5 mL of distilled water per gram of pollen. After centrifugation for 5 min at 13 000×g, the clear supernatant was divided into small aliquots and stored at −20° C. until use. The pollen extract was subjected to reducing SDS-PAGE and either stained with Coomassie Brilliant Blue or electroblotted onto nitrocellulose membrane. Protein blots were blocked for 1 hr at room temperature using either 1% (v/v) Tween-20 in PBS (137 mM NaCl, 2.7 mM KCl, 4.3 mM $Na_2HPO_4$, 1.4 mM $KH_2PO_4$) or 5% (w/v) defatted dry milk in PBS and then incubated overnight with patient serum diluted five-fold in PBS containing 0.1% Tween-20. After washing in the same buffer, bound IgE was visualized using a rabbit anti-IgE antiserum followed by horseradish peroxidase-conjugated donkey anti-rabbit IgG and ECL detection.

Protein Sequencing

An IgE-binding protein band corresponding to Phl p 11 was identified by immunoblotting using an essentially monoreactive serum sample. The band was excised from a Coomassie Brilliant Blue-stained SDS-polyacrylamide gel, homogenized and extracted in 6 M guanidinium hydrochloride. After removal of polyacrylamide fragments by centrifugation, the extracted protein was subjected to 20 cycles of sequencing from the N-terminus using a Hewlett-Packard G1000A instrument.

Cloning and Characterization of Phl p 11 cDNA

First-strand cDNA was synthesized from purified poly-$A^+$ RNA using the primer 5'-CCA GTG AGC AGA GTG ACG AGG ACT CGA GCT CAA GC(T)18-3' (QT; SEQ ID NO:19). For 3'-PACE, the two nested specific forward primers GSP-1 (5'-CAT TAC ATA TGG ACA AGG GCC CSG GCT TCG TSG TSA C-3'; SEQ ID NO:15) and GSP-2 (5'-CAT GAA TTC GGA CGC GTC TAC TGC GAC-3'; SEQ ID NO:20) were used, together with the two nested universal reverse primers $Q_o$ (5'-CCA GTG AGC AGA GTG ACG-3'; SEQ ID NO:21) and $Q_1$ (5'-GAG GAC TCG AGC TCA AGC-3'; SEQ ID NO:22). Primers GSP-1 and GSP-2 were designed from the N-terminal amino acid sequence of the Phl p 11 protein while primers $Q_o$ and $Q_1$ were identical to adjacent parts of cDNA synthesis primer QT.

First-strand cDNA was synthesized from purified poly-$A^+$ RNA using the primer 5'-CCA GTG AGC AGA GTG ACG AGG ACT CGA GCT CAA $GC(T)_{18}$-3' ($Q_T$). For 3'-RACE, the two nested specific forward primers GSP-1 (5'-CAT TAC ATA TGG ACA AGG GCC CSG GCT TCG TSG TSA C-3') and GSP-2 (5'-CAT GAA TTC GGA CGC GTC TAC TGC GAC-3') were used, together with the two nested universal reverse primers $Q_O$ (5'-CCA GTG AGC AGA GTG ACG-3') and $Q_I$ (5'-GAG GAC TCG AGC TCA AGC-3'). Primers GSP-1 and GSP-2 were designed from the N-terminal amino acid sequence of the Phl p 11 protein while primers $Q_O$ and $Q_I$ were identical to adjacent parts of cDNA synthesis primer $Q_T$.

To generate a Phl p 11-enriched template for 3'-RACE, second-strand cDNA was synthesized by 40 cycles of primer extension of biotinylated GSP-1 using first-strand cDNA as template. The cycling profile used was: 95° C./5 min, followed by 40 cycles of 95° C./60 sec, 58° C./60 sec, 72° C./90 sec. The product of this reaction was then immobilized on streptavidin-modified magnetic beads and washed with 0.1 M NaOH and TE (10 mM Tris-HCl, 1 mM EDTA, pH 8.0). In the first round of 3'-RACE, a sample of immobilized second-strand cDNA and primers GSP-1 and $Q_O$ were used in the cycling profile: 95° C./5 min, followed by 40 cycles of 95° C./1 min, 72° C./2 min. One µl of a 20-fold dilution of this reaction was used as template together with primers GSP-2 and $Q_I$ in the second round of 3'-RACE, with the cycling profile: 95° C./5 min, followed by 30 cycles of 95° C./60 sec, 58° C./60 sec, 72° C./90 sec. The GSP-2 and $Q_I$ primers were designed to incorporate EcoRI and HindIII sites, respectively, at the ends of the amplification product. After purification and cleavage with these enzymes, the product was cloned between the EcoRI and HindIII sites of pBR322 (22). Five candidate clones were subjected to DNA sequencing, revealing a single open reading frame corresponding to Phl p 11.

Amplification of full-length Phl p 11 coding sequence from immobilized second-strand cDNA was performed using the GSP-1 primer and the reverse primer PP 11/R-X (5'-AGT CAC TCG AGT GGC GTC TCG GGG GCG TC-3'; SEQ ID NO:18), which was based on the 3' end of the Phl p 11 open reading frame. These two primers were designed to incorporate terminal NdeI and XhoI sites, respectively, in the PCR product. The then-nocycling profile used in this reaction was the same as that in round two of the 3'-RACE experiment. The amplification product, purified and digested with NdeI and XhoI, was cloned between the NdeI and XhoI sites of a pET-23a(+)—derivative designed for expression of the gene of interest as a fusion to the maltose binding protein (MBP) of *E. coil*. The resulting full-length construct for expression was verified by DNA sequencing.

Expression and Purification of rPhl p 11

The *P. pratense* allergen was expressed in *E. coli* as a fusion to MBP. Plasmid DNA from one selected clone was introduced into strain BL21 harboring plasmid pT7POL23 which provides T7 RNA polymerase in a stringently controlled, temperature-dependent manner (18). LB medium (10 g/L tryptone, 5 g/L yeast extract, 5 g/L NaCl, adjusted to pH 7.0 using 1 M NaOH) was inoculated 1:500 with an overnight culture and first grown at 30° C. to mid-log phase. The incubation temperature was then raised to 42° C. for 1 hr, followed by 4 hrs at 30° C. before harvest. Cells were collected by centrifugation at 10 000×g for 10 min at 4° C. and resuspended in 5 mL of buffer A (20 mM Tris-HCl pH 8.0, 0.5 M NaCl, 100 mM β-mercaptoethanol, 5 mM imidazole) per gram (fresh weight) of cells. The resuspended cells were ruptured by sonication while kept on ice, followed by centrifugation to remove solid material. Following exchange to buffer B (20 mM Tris-HCl pH 8.0, 0.5 M NaCl, 5 mM β-mercaptoethanol) containing 5 mM imidazole using Sephadex G-25, the supernatant was loaded onto a $Ni^{2+}$-charged 5 mL HiTrap Chelating column for IMAC. The column was washed with 20 mM imidazole in buffer B and elution was performed with a 20-250 mM gradient of imidazole in buffer B. Fractions containing the eluted fusion protein were pooled and subjected to a final step of size exclusion chromatography through Superdex 75, equilibrated with non-reducing buffer, to obtain a homogeneous, unaggregated preparation without visible contamination by *E. coli* proteins. To serve as a negative control in functional studies, MBP alone was expressed from BL21[pT7POL23] cells harboring the expression vector without insert and the protein purified as above, except that buffer B containing 5 mM imidazole was used in place of buffer A at the stage of cell homogenization. The concentration of MBP-Phl p 11 and MBP in the final preparations was determined from their absorbance at 280 run, using calculated extinction coefficients of 1.30 and 1.47 per mg/mL, respectively.

Assessment of IgE-Binding Activity of rPhl p 11 Using Pharmacia CAP System

In vitro IgE-binding activity of the purified recombinant allergen was examined in Pharmacia CAP System, an immunoassay system used for IgE antibody detection in clinical diagnosis of atopic allergy. Experimental ImmunoCAP tests were prepared by covalent immobilization of the purified allergen onto activated cellulose at a concentration chosen to achieve an adequate linear measuring range and a background for negative sera adequately below the conventional cut-off value of 0.35 kU$_A$/L. Negative control tests carrying MBP alone were prepared using the same protein concentration at immobilization. For determination of specific IgE to the whole complement of natural *P. pratense* pollen proteins, the regular pollen extract-based ImmunoCAP test was used. For the purpose of comparison to a previously established recombinant allergen, all serum assays were run in parallel with rPhl p 2 ImmunoCAP tests. Assay controls and calculation of statistical parameters attesting to the quality of the assays were performed using standard assay system routines and software (Pharmacia Diagnostics).

Immunoblot Analysis of IgE Binding Properties of rPhl p 11

The proportion of timothy grass pollen-specific IgE directed against rPhl p 11 and rPhl p 5 was investigated by a RAST inhibition-based experiment. Serum samples from 10 rPhl p 11-reactive subjects were diluted 1:10 in buffer C (50 mM sodium phosphate pH 7.5, 0.5% (v/v) Tween 20, 0.5% (w/v) BSA, 0.05% (w/v) NaN$_3$) and preadsorbed overnight at 4° C. with either rPhl p 11, MBP (negative control) or rPhl p 5 (positive control), all at a final concentration of 10 μg/mL. To ensure conditions of antigen excess on the solid phase, approximately 0.2 mg of natural timothy grass pollen protein extract was immobilized to nitrocellulose strips of exactly the same size (0.6×3 cm). Strips were blocked by preincubation with buffer C (once for 1 hour and twice for 5 minutes) and then exposed to the preadsorbed sera at 4° C. overnight. The following day, strips were washed four times in buffer C and then probed with $^{125}$I-labeled anti-human IgE antibody at room temperature overnight. Strips were washed again four times in buffer C and dried. The amount of $^{125}$I-labeled anti-human IgE antibody was determined using a gamma counter (Wallac, Turku, Finland). The percentage inhibition of IgE binding after preincubation of sera with rPhl p 5 or rPhl p 11 was calculated as follows: % inhibition=100–100×(cpm rPhl p 5/cpm MBP or rPhl p 11/cpm MBP).

The capacity of the recombinant allergen to bind Phl p 11-specific IgE antibodies was studied by IgE immunoblot inhibition experiments (17). Sera from two grass pollen allergic subjects with IgE reactivity to rPhl p 11 were preadsorbed with purified rPhl p 11 at 10 μg/mL serum, or, for control purposes, with an equal concentration of MBP or BSA. Preadsorbed sera were exposed to nitrocellulose-blotted timothy grass pollen proteins separated by SDS-PAGE and bound IgE was detected as described (17).

Histamine Release Experiments

Granulocytes were isolated by dextran sedimentation of heparinized blood samples (23, 24) from two grass pollen allergic and one non-allergic individuals. Aliquots of washed cells were incubated with a range of concentrations (0.001 μg/mL, 0.01 μg/mL, 0.1 μg/mL, 1 μg/mL) of purified rPhl p 11, MBP, and a monoclonal anti-IgE antibody. Histamine released in the supernatant was measured by radioimmunoassay. Total histamine was determined after freeze-thawing of cells. Results were displayed as mean values of triplicate determinations and represent the percentage of total histamine.

Skin Testing

After informed consent was obtained from two grass pollen-allergic and four non-allergic individuals, skin prick tests were performed on their forearms as described (25). Individuals were pricked with 20 μl aliquots of solutions containing different concentrations (0.1 μg/mL, 1 μg/mL, 10 μg/mL, 100 μg/mL) of purified rPhl p 11 and MBP, and with timothy grass pollen extract, histamine and sodium chloride. The skin reactions were recorded 20 minutes after sample application by photography and by transferring a ballpoint pen-tracing of the wheal area to paper using adhesive tape. Mean wheal diameters (Dm) were determined as follows: Dm=0.5×(D1+D2) where D1 and D2 represent the largest longitudinal and transverse diameters in mm, respectively.

Results

Immunochemical Detection, Isolation and Protein Sequencing of Natural Phl p 11

Immunoblot analysis of serum from a grass pollen-allergic subject, which lacked IgE antibodies to all purified or recombinant allergens from *P. pratense* currently available (rPhl p 1, rPhl p 2, nPhl p 4, rPhl p 5, rPhl p 6, rPhl p 7, and rPhl p 12), revealed predominant IgE binding to a single protein band at approximately 20 kDa. One faint band in Coomassiestained SDS-PAGE aligned perfectly with the IgE-reactive band in the immunoblot analysis (FIG. 1), although a more abundant protein of slightly smaller size could not unambiguously be ruled out. Protein from both these bands was extracted separately and a portion of each applied to nitrocellulose membrane for dot-blot analysis. Incubation with the reactive senim and subsequent IgE detection allowed a positive identification of the band of slightly higher MW as the target for IgE antibodies present in the serum sample (not shown). The extracted protein was subjected to N-terminal sequencing and the following 20-residue determination was obtained: DKGPGFVVT-GRVYCDPCRAG (residues 1-20 of SEQ ID NO:2). A database search for homologous sequences revealed an exact match to the rye grass allergen Lol p 11, previously purified and amino acid sequenced by van Ree et al. (26).

cDNA Cloning and Sequence Analysis of Phl p 11

After back-translation of the N-terminal amino acid sequence into DNA, using the codon preference seen in other genes expressed in *P. pratense* pollen, two nested forward PCR primers (GSP-1 and GSP-2) were designed for use in 3'-RACE and RT-PCR. First-strand cDNA was synthesized from a poly-A$^+$ RNA preparation, using a universal oligo-dT primer carrying terminal target sequence for two nested reverse PCR primers, $Q_O$ and $Q_T$, to be used in subsequent steps of amplification. Specifically enriched second-strand cDNA, generated by 40 cycles of primer extension of GSP-1 on first-strand cDNA, was used as template in the first round of 3'-RACE, carried out with primers GSP-1 and $Q_O$. In a second round, 1/1000 of the first round reaction was used as template together with primers GSP-2 and $Q_T$. Analysis of this reaction by agarose gel electrophoresis revealed two distinct bands of similar intensity, approximately 700 and 800 bp in size (not shown). The use of raised annealing temperature did not change the appearance of the second round 3'-RACE product. The double-band product was therefore tentatively considered genuine and specific. The product was cloned and transformants harboring inserts matching both fragment sizes were identified and analyzed by DNA sequencing. All five clones examined contained inserts of nearly identical sequence and it appeared that the difference in size between the two bands seen after the second round of 3'-RACE was due to alternative sites for priming of cDNA synthesis (FIG. 2), possibly as a result of heterogeneity in the site of transcript polyadenylation. All clones contained an identical open reading frame with a codon usage that agreed well with that of previously known genes expressed in *P. pratense* pollen. Beyond the observed stop codon, none of the three forward reading frames displayed codons that fulfilled this criterion. In order to obtain a cDNA encoding the full-length polypeptide, an RT-PCR reaction was performed using forward primer GSP-1 and reverse primer PP11/R-X, the latter designed from the 3' end of the open reading frame. The product of this reaction, which appeared as a single band in agarose gel electrophoresis, was cloned in an expression vector and its sequence confirmed.

The open reading frame of the cDNA defined a polypeptide of 143 amino acid residues with a calculated isoelectric point of 4.8, a molecular mass of 15.8 kDa and one potential site for N-linked glycosylation (FIG. 2). A similarity search through the databases available at NCBI (www.ncbi.nlm.nih.gov) identified pollen proteins from a range of mono- and dicotyledonous plant species with sequence homology to the polypeptide deduced from the cDNA sequence. These included *Lolium perenne* (rye grass), *Phalaris coerulescens* (canary grass), *Oryza sativa* (rice), *Zea mays* (maize), *Betula pendula* (birch), *Arabidopsis thaliana*, *Lycopersicon esculentum* (tomato), *Olea europaea* (olive), *Syringa vulgaris* (lilac) and *Ligustrum vulgare* (privet). The level of amino acid sequence identity within this family of pollen proteins ranged from 32% to 95% and an alignment, displaying secondary structure predictions and conserved features, is shown in FIG. 3. From the sequence comparisons it is clear that the *P. pratense* allergen is a counterpart of the *L. perenne* allergen Lol p 11 and should therefore be designated Phl p 11.

The most prominent difference in primary structure observed between Phl p 11 and Lol p 11 (sequence accession No. A54002) was a stretch of nine additional amino acid residues (-DLRDAPETP; residues 135-143 of SEQ ID NO:2) at the C-terminus of Phl p 11, equivalent to a 1.0 kDa increment in molecular mass. In comparison to the *L. perenne* homologue, the Phl p 11 sequence contained a total of six amino acid substitutions, four of which were non-conservative (D42N, K56G, D57L, K83T). At position 103, which was not determined in the case of Lol p 11, an asparagine residue was present in the Phl p 11 sequence. The two homologues showed conservation of one potential site for N-linked glycosylation (residue 24) and six cysteine residues.

As previously shown by van Ree et al. (26), group 11 grass pollen allergens are structurally related to the soybean trypsin inhibitor and may therefore present antigenic structures similar to proteins belonging to this family. Very recently, structurally related allergens from English plantain, *Plantago lanceolata*, (Pla 11) and goosefoot, *Chenopodium album*, (Che a 1) were reported (27, 28).

The discrepancy between the observed apparent MW of the native Phl p 11 allergen by SDS-PAGE and the MW calculated from the deduced amino acid sequence is presumably explained by post-translational modification of the native allergen. In support of this is the report by van Ree et al. (26), where the homologous *L. perenne* protein was shown to carry N-linked glycosylation amounting to approximately 8% of the total molecular mass, and the conservation of the corresponding glycan attachment site in the amino acid sequence of Phl p 11.

Expression in *Escherichia coli* and Purification of rPhl p 11

With the aim of allergenic and serological characterization of the Phl p 11 allergen, the protein was expressed in *E. coli* and purified to homogeneity. Because of poor solubility when the allergen was initially expressed with an N-terminal hexahistidine tag as the only engineered addition, we chose instead to produce it as a fusion to the *E. coli* maltose binding protein as a means to aid solubility. After preparing a construct where transcription of the fusion was under control of the T7 promoter, using *E. coli* XL1-Blue as a cloning host, the plasmid was transferred to strain BL21 harboring plasmid pT7POL23. In this binary system the construct is quiescent at 30° C. and recombinant protein expression induced by a temperature shift to 42° C. (FIG. 4).

Using this strain for expression, accumulation of MBP-Phl p 11 to approximately 10% of total cellular protein was obtained, as estimated from Coomassie-stained SDS-PAGE (FIG. 4). Analysis of fractionated cellular material revealed that approximately half of the fusion protein was present in the soluble phase (not shown). The proportion of soluble protein tended to be higher when the culture had been returned to 30° C. after a period of induction at 42° C., as opposed to being kept at 42° C. until harvest (not shown). In order to minimize aggregation of the soluble fusion protein, post-harvest processing was performed under reducing conditions. After buffer exchange to lower the concentration of reductant in the cleared cell extract, the protein was subjected to a first step of purification by IMAC. While the eluted material appeared as a single distinct band of the expected size on reducing SDS-PAGE, analytical gel filtration indicated the presence of different aggregation forms in addition to the monomer. A step of size exclusion chromatography using Superdex 75 was therefore added to the purification process. The final preparation appeared monomeric by analytical gel filtration and free of contaminating bacterial proteins by SDS-PAGE. It appeared stable and no formation of aggregates was observed upon storage at −20° C. The final yield of purified protein was 12 mg per liter of bacterial culture, or 1.7 mg per gram of cell pellet (fresh weight).

Analysis of Antibody Recognition of rPhl p 11

To examine the IgE antibody binding capacity of the recombinant allergen and investigate the frequency and magnitude of Phl p 11-specific IgE sensitization among grass pollen-allergics, serological tests were prepared for use in Pharmacia CAP System. As a control for antibody binding to the MBP part of the fusion protein, tests carrying MBP alone were prepared and used in parallel. Upon analysis of serum samples of 184 grass pollen-sensitized subjects using these tests, 59 (32%) of them were found to contain specific IgE reactivity to the recombinant allergen (Table II). The average level of IgE to rPhl p 11 in the specifically reactive sera was 16 $kU_A/L$, as compared to 79 $kU_A/L$ of IgE to natural extract of *P. pratense* pollen. Thus, it appears that on average among these subjects, approximately 20% of the IgE reactivity to *P. pratense* pollen allergens was directed to rPhl p 11.

In two of the sera that showed a positive result with the rPhl p 11 test, there was also an apparent binding of IgE to MBP alone. For one of these sera the IgE determination was in fact higher with the MBP test, and this serum was therefore regarded as lacking IgE to rPhl p 11. For the other serum, the contribution by MBP to the IgE binding by the fusion protein was only about 1%, which was considered insignificant. In total, only four sera of all 184 tested (2%) showed detectable IgE binding to MBP alone, indicating that MBP may be a suitable fusion partner for recombinant allergen production in instances when a soluble non-fusion protein cannot be efficiently produced in *E. coli*.

For the purpose of comparison, the 184 serum samples were also tested with an assay specific for a previously established major grass pollen allergen, rPhl p 2. IgE antibody reactivity directed to this allergen was found in 103 (56%) of all tested subjects, with an average IgE level of 11.4 kU$_A$/L. Binding to rPhl p 2 would thereby account for approximately 15% of the total level of IgE to whole, natural extract of *P. pratense* pollen in this subset of sera, which was 74 kU$_A$/L on average. In summary, the serological analysis shows that the *E. coli*-expressed rPhl p 11 has significant and specific IgE antibody binding capacity, comparable in frequency and magnitude to that of rPhl p 2.

Inhibition of IgE Binding to Natural Grass Pollen Extract by Soluble rPhl p 11

To compare in a more direct way the IgE binding characteristics of recombinant and natural Phl p 11, an immunoblot inhibition experiment was performed. In this analysis, competition for IgE binding to immobilized natural allergen by soluble rPhl p 11 would be visualized as attenuation of IgE binding to immobilized natural Phl p 11 after preincubation of patient serum with the recombinant allergen. As a control for unspecific inhibition, both serum samples used were preincubated with BSA and MBP in parallel with the rPhl p 11 pretreatment. While the control proteins had no visible effect on IgE binding to extract proteins, as compared to preincubation with buffer (not shown), pretreatment of the serum samples with rPhl p 11 almost completely abolished the autoradiography signal at 20 kDa molecular weight (FIG. 5). The result demonstrated that the recombinant protein shared epitopes for human IgE antibodies with natural Phl p 11.

The contribution of Phl p 11 to the total IgE binding activity of pollen proteins was further examined by dot blot inhibition experiments in which rPhl p 5, an allergen known for its high IgE binding capacity (7), was used for comparison. Equal amounts of pollen protein extract were spotted onto identical pieces of nitrocellulose membrane and exposed to patients' sera that had been preincubated with either rPhl p 11, rPhl p 5 or MBP. From serological analyses, these sera were known to contain IgE to both Phl p 11 and Phl p 5, but not to MBP. As controls, buffer incubation and serum from one non-allergic individual were used. After washing, membrane-bound IgE was determined radiometrically and the inhibition effects of rPhl p 11 and rPhl p 5 were calculated in relation to the MBP-pretreated samples. The results of the experiment are shown in Table III. On average rPhl p 11 was found to inhibit 25% of the IgE binding to pollen extract, which corresponds to the quantitative serological data shown in Table II, while rPhl p 5 caused an average inhibition of 55%. We conclude that Phl p 11 accounts for a relevant proportion of timothy grass pollen-specific IgE antibodies, although smaller than Phl p 5.

rPhl p 11 Induces Basophil Histamine Release and Immediate Skin Reaction

In an experiment on basophils from a high-level Phl p 11-sensitized allergic individual, rPhl p 11 induced dose-dependent release of histamine, demonstrating its capacity to productively cross-link cell surface-bound IgE antibodies. Limited histamine release occurred from cells of a low-grade Phl p 11-sensitized subject and none from cells of a non-allergic upon incubation with rPhl p 11. (Table 1). Evidence of specific biological activity of rPhl p 11 in vivo was obtained from skin test experiments. In two sensitized subjects, dose-dependent wheal reactions resulted from challenge with a dilution series of the allergen while no reaction occurred in four non-allergic controls tested. (Table 2). The rPhl p 11 fusion partner MBP alone gave rise to no reaction in neither these experiments. Hence, rPhl p 11 exhibited biological activity which fulfilled criteria of specificity.

TABLE 1

Specific induction of histamine release from basofils by rPhl p 11[a]

| | Patient A | | | Patient B | | | Patient C | | |
|---|---|---|---|---|---|---|---|---|---|
| Conc (μg/ml) | MBP | MBP-rPhl p 11 | anti-IgE | MBP | MBP-rPhl p 11 | Anti-IgE | MBP | MBP-rPhl p 11 | anti-IgE |
| 0 | 6.5 | 6.7 | 6.6 | 6.5 | 6.5 | 6.5 | 3.5 | 3.5 | 3.5 |
| 0.001 | 5.8 | 16 | 11.3 | 5.5 | 5.5 | 8.25 | 3.5 | 3.5 | 8.25 |
| 0.01 | 5.2 | 29 | 16 | 5.5 | 5.8 | 10 | 3.4 | 3.5 | 14 |
| 0.1 | 4.9 | 34 | 28.5 | 5.4 | 7.8 | 23 | 3.5 | 3.8 | 43 |
| 1 | 4.7 | 36.5 | 34 | 5.3 | 7.8 | 13 | 3.5 | 3.5 | 55 |

[a]Release of histamine is expressed as percentage of the cells' total content of histamine.

TABLE 2

Skin prick tests with rPhl p 11[b]

| | MBP-rPhl p 11 | | | | | | |
|---|---|---|---|---|---|---|---|
| Subject | 100 μg/ml | 10 μg/ml | 1 μg/ml | 0.1 μg/ml | MBP all conc | Pollen extract | Histamine |
| Allergic No. 1 | 5.5 | 2.5 | — | — | — | 9.0 | 3.6 |
| Allergic No. 2 | 8.0 | 5.5 | 4.0 | — | — | 10.5 | 7.0 |
| Non-allergic No. 1 | — | — | — | — | — | — | 8.0 |
| Non-allergic No. 2 | — | — | — | — | — | — | 7.5 |
| Non-allergic No. 3 | — | — | — | — | — | — | 4.9 |
| Non-allergic No. 4 | — | — | — | — | — | — | 8.5 |

[b]Two allergics and four non-allergics were skin tested with rPhl p 11 at different concentrations, with timothy grass pollen extract and histamine. The diameter of the resulting wheal reactions were determined and are presented in mm.

Discussion

Grass pollens belong to the most frequently sensitizing and potent allergen sources. They contain a number of allergenic molecules, several of which have been identified and characterized in the recent past (3). In the present invention we report the identification, cloning and recombinant production of a novel *P. pratense* pollen allergen which adds new important epitopes to the growing panel of recombinant grass pollen allergens (29).

Despite the fact that the group 11 grass pollen allergens are glycoproteins (26) and contain several cysteine residues, we were able to produce soluble, monomeric and immunologically active rPhl p 11 allergen by utilizing MBP as a fusion partner for expression in E. coli. Extensive serological characterization of IgE reactivity to rPhl p 11 was carried out using a quantitative assay system where allergen is covalently immobilized onto activated cellulose. Using the rPhl p 11-specific tests, we found that about one third of all grass pollen sensitized subjects analyzed (n=184) contained serum IgE antibodies binding to rPhl p 11 and that the magnitude of binding corresponded to a significant proportion of grass pollen-specific IgE antibodies in these subjects.

Evidence supporting the authenticity of epitope presentation by rPhl p 11 was obtained from immunoblot inhibition experiments, where natural grass pollen proteins were attached on solid phase and rPhl p 11 used as fluid-phase inhibitor. Specific and extensive inhibition of IgE binding to the natural allergen occurred in both of two patient sera examined, demonstrating that rPhl p 11 could compete with natural Phl p 11 for IgE antibody binding. Taken together, the serological data show that immunoreactive rPhl p 11 can be produced using E. coli expression and that the recombinant protein shares epitopes for IgE antibodies with the natural allergen. Based on the results obtained, it is clear that rPhl p 11 represents an important addition to the panel of recombinant grass pollen allergens useful for in vitro diagnosis of grass pollen allergy.

Relevant to this discussion is the immunological analysis of chemically deglycosylated natural Lol p 11 reported by van Ree et al. (26), which suggested the involvement of carbohydrate structures in the IgE binding properties of this allergen. Thus, we cannot exclude that a qualitative difference in allergenic properties exists between natural Phl p 11 and the recombinant molecule described in this paper and that expression of Phl p 11 in a glycosylated form, using a eukaryotic host, could yield a recombinant allergen with different IgE binding characteristics. On the other hand, in view of recent notions that glycan epitopes may not be efficient elicitors of IgE-mediated reactions or informative in relation to clinical allergy manifestation (30-34), it is possible that an unmodified recombinant allergen expressed in E. coli is more useful for diagnostic purposes.

Despite the significant sequence homology among the members of the widely represented (grasses, trees and weeds) group of allergens exemplified by Phl p 11 in timothy grass and Ole e 1 in olive tree pollen, little cross-reactivity for IgE antibodies appears to exist between them. In a preliminary analysis, we have been unable to detect cross-reaction between rPhl p 11 and Ole e 1 (Niederberger, Valenta & Lidholm, unpublished data) and the results of recent studies on other members of this allergen family (27, 28) are in agreement with this observation.

One important implication of the apparent lack of significant cross-reactivity between rPhl p 11 and other members of this allergen family is that they are useful as diagnostic markers to more precisely identify the primary sensitizer of allergic individuals, as compared to natural extracts or cross-reactive components such as profilin, two-EF-hand allergens or Bet v 1 homologues. Thus, a preferential IgE recognition of Phl p 11, in relation to other members of this allergen family, may suggest a primary sensitization by grass pollen rather than another allergen source containing cross-reactive components. The use of selected recombinant allergens in this way may provide information useful for advice on allergen avoidance and adequate selection of allergen extract for specific immunotherapy treatment.

In conclusion, the present invention concerns cDNA cloning and recombinant production of an IgE-reactive and biologically active group 11 grass pollen allergen. Recombinant Phl p 11 can be used to identify group 11 allergen sensitization in patients and for specific immunotherapy.

REFERENCES

1. Kay, A. B. 1997. Allergy and Allergic Disease. Blackwell Science, Oxford.
2. D'Amato, G., F. T. Spieksma, G. Liccardi, S. Jäger, M. Russo, K. Kontou-Fili, H. Nikkels, B. Wüthrich, and S. Bonini. 1998. Pollen-related allergy in Europe. *Allergy* 53:567.
3. Esch, R. E. 1999. Grass pollen allergens. In *Allergens and Allergen Immunotherapy*. R. F. Lockey, and S. C. Bukantz, eds. Marcel Dekker, Inc., NY, p. 103.
4. Laffer, S., R. Valenta, S. Vrtala, M. Susani, R. van Ree, D. Kraft, O. Schneider, and M. Duchêne. 1994. Complementary DNA cloning of the major allergen Phl p I from timothy grass (*Phleum pratense*); recombinant Phl p I inhibits IgE binding to group I allergens from eight different grass species. *J. Allergy Clin. Immunol.* 94:689.
5. Petersen, A., G. Schramm, A. Bufe, M. Schlaak, and W.-M. Becker. 1995. Structural investigations of the major allergen Phl p I on the complementary DNA and protein level. *J. Allergy Clin. Immunol.* 95:987.
6. Dolecek, C., S. Vrtala, S. Laffer, P. Steinberger, D. Kraft, O. Scheiner, and R. Valenta. 1993. Molecular characterization of Phl p II, a major timothy grass (*Phleum pratense*) pollen allergen. *FEBS Lett.* 335:299.
7. Vrtala, S., W. R. Sperr, I. Reimitzer, R. van Ree, S. Laffer, W. D. Müller, P. Valent, K. Lechner, H. Rumpold, D. Kraft, O. Scheiner, and R. Valenta. 1993. cDNA cloning of a major allergen from timothy grass (*Phleum pratense*) pollen; characterization of the recombinant Phl p V allergen. *J. Immunol.* 151:4773.
8. Bufe, A., W.-M. Becker, G. Schramm, A. Petersen, U. Mamat, and M. Schlaak. 1994. Major allergen Phl p Va (timothy grass) bears at least two different IgE-reactive epitopes. *J. Allergy Clin. Immunol.* 94:173.
9. Bufe, A., G. Schramm, M. B. Keown, M. Schlaak, and W.-M. Becker. 1995. Major allergen Phl p Vb in timothy grass is a novel pollen RNase. *FEBS Lett.* 363:6.
10. Petersen, A., A. Bufe, G. Schramm, M. Schlaak, and W.-M. Becker. 1995. Characterization of the allergen group VI in timothy grass pollen (Phl p 6). II. cDNA cloning of Phl p 6 and structural comparison to grass group V. *Int. Arch. Allergy Immunol.* 108:55.
11. Vrtala, S., S. Fischer, M. Grote, L. Vangelista, A. Pastore, W. R. Sperr, P. Valent, R. Reichelt, D. Kraft, and R. Valenta. 1999. Molecular, immunological, and structural characterization of Phl p 6, a major allergen and P-particle-associated protein from timothy grass (*Phleum pratense*) pollen. *J. Immunol.* 163:5489.
12. Niederberger, V., B. Hayek, S. Vrtala, S. Laffer, A. Twardosz, L. Vangelista, W. R. Sperr, P. Valent, H. Rumpold, D. Kraft, K. Ehrenberger, R. Valenta, and S. Spitzauer. 1999. Calcium-dependent immunoglobulin E recognition of the apo- and calcium-bound form of a cross-reactive two EF-hand timothy grass pollen allergen, Phl p 7. *FASEB J.* 13:843.
13. Valenta, R., T. Ball, S. Vrtala, M. Duchêne, D. Kraft, and O. Scheiner. 1994. cDNA cloning and expression of timothy grass (*Phleum pratense*) pollen profilin in

*Escherichia coli*: comparison with birch pollen profilin. *Biochem. Biophys. Res. Commun.* 199:106.

14. Suck, R., A. Petersen, S. Hagen, 0. Cromwell, W. Becker, and H. Fiebig. 2000. Complementary DNA cloning and expression of a newly recognized high molecular mass allergen Phl p 13 from timothy grass pollen (*Phleum pratense*). *Clin. Exp. Allergy* 30:324.

15. Niederberger, V., S. Laffer, R. Fröschl, D. Kraft, H. Rumpold, S. Kapiotis, R. Valenta, and S. Spitzauer. 1998. IgE antibodies to recombinant pollen allergens (Phl p 1, Phl p 2, Phl p 5, Bet v 2) account for a high percentage of grass pollen-specific IgE. *J. Allergy Clin. Immunol.* 101:258.

16. Valenta, R., M. Duchêne, K. Pettenburger, C. Sillaber, P. Valent, P. Bettelheim, M. Breitenbach, H. Rumpold, D. Kraft, and O. Scheiner. 1991. Identification of profilin as a novel pollen allergen; IgE autoreactivity in sensitized individuals. *Science* 253:557.

17. Valenta, R., M. Duchêne, C. Ebner, P. Valent, C. Sillaber, P. Deviller, F. Ferreira, M. Tejkl, H. Edelmann, D. Kraft, and O. Scheiner. 1992. Profilins constitute a novel family of functional plant pan-allergens. *J. Exp. Med.* 175:377.

18. Mertens, N., E. Remaut, and W. Fiers. 1995. Tight transcriptional control mechanism ensures stable high-level expression from T7 promoter-based expression plasmids. *Bio/Technology* 13:175.

19. Ball, T., W. R. Sperr, P. Valent, J. Lidholm, S. Spitzauer, C. Ebner, D. Kraft, and R. Valenta. 1999. Induction of antibody responses to new B cell epitopes indicates vaccination character of allergen immunotherapy. *Eur. J Immunol.* 29:2026.

20. Chirgwin, J. M., A. E. Przybyla, R. J. MacDonald, and W. J. Rutter. 1979. Isolation of biologically active ribonucleic acid from sources enriched in ribonuclease. *Biochemistry* 18:5294.

21. Frohman, M. A. 1993. Rapid amplification of complementary DNA ends for generation of full-length complementary DNAs: thermal RACE. *Methods Enzymol.* 218:340.

22. Bolivar, F., R. L. Rodriguez, P. J. Greene, M. C. Betlach, H. L. Heyneker, and H. W. Boyer. 1977. Construction and characterization of new cloning vehicles. II. A multipurpose cloning system. *Gene* 2:95.

23. Valent, P., J. Besemer, M. Muhm, O. Majdic, K. Lechner, and P. Bettelheim. 1989. Interleukin 3 activates human blood basophils via high-affinity binding sites. *Proc. Natl. Acad. Sci. U.S.A.* 86:5542.

24. Valenta, R., W. R. Sperr, F. Ferreira, P. Valent, C. Sillaber, M. Tejkl, M. Duchêne, C. Ebner, K. Lechner, D. Kraft, and O. Scheiner. 1993. Induction of specific histamine release from basophils with purified natural and recombinant birch pollen allergens. *J. Allergy Clin. Immunol.* 91:88.

25. Vrtala, S., K. Hirtenlehrer, L. Vangelista, A. Pastore, H.-G. Eichler, W. R. Sperr, P. Valent, C. Ebner, D. Kraft, and R. Valenta. 1997. Conversion of the major birch pollen allergen, Bet v 1, into two non-anaphylactic T-cell epitope-containing fragments: candidates for a novel form of specific immunotherapy. *J. Clin. Invest.* 99:1673.

26. van Ree, R., D. R. Hoffinan, W. van Dijk, V. Brodard, K. Mahieu, C. A. M. Koeleman, M. Grande, W. A. van Leeuwen, and R. C. Aalberse. 1995. Lol p XI, a new major grass pollen allergen, is a member of a family of soybean trypsin inhibitor-related proteins. *J. Allergy Clin. Immunol.* 95:970.

27. Calabozo, B., A. Diaz-Peralez, G. Salcedo, D. Barber, and F. Polo. 2001. Structural and antigenic similarity between Pla 11 and Ole e 1, the major allergens of English plantain and olive pollens. *J. Allergy Clin. Immunol.* 107:515.

28. Barderas, R., M. Villalba, R. Monsalve, E. Batanero, E. Gonzalez, S. Huecas, I. Cuesta, O. Palomares, P. Barral, and R. Rodriguez. 2001. Isolation and cloning of Che a 1, allergen from *Chenopodium album* pollen. *J. Allergy Clin. Immunol.* 107:S19.

29. Valenta, R., J. Lidholm, V. Niederberger, B. Hayek, D. Kraft, and H. Gronlund. 1999. The recombinant allergen-based concept of component-resolved diagnostics and immunotherapy (CRD and CRIT) [Review]. *Clin. Exp. Allergy* 29:896.

30. van der Veen, M. J., R. van Ree, R. C. Aalberse, J. Akkerdaas, S. J. Koppelman, H. M. Jansen, and J. S. van der Zee. 1997. Poor biologic activity of cross-reactive IgE directed to carbohydrate determinants of glycoproteins. *J. Allergy Clin. Immunol.* 100:327.

31. Aalberse, R. C., and R. van Ree. 1997. Crossreactive carbohydrate determinants. *Clin. Rev. Allergy Immunol.* 15:375.

32. Aalberse, R. C. 1998. Clinical relevance of carbohydrate allergen epitopes. *Allergy* 53:54.

33. Mari, A., P. Iacovacci, C. Affemi, B. Barletta, R. Tinghino, G. Di Felice, and C. Pini. 1999. Specific IgE to cross-reactive carbohydrate determinants strongly affect the in vitro diagnosis of allergic diseases. *J. Allergy Clin. Immunol.* 103:1005.

34. van Ree, R., and R. C. Aalberse. 1999. Specific IgE without clinical allergy. *J. Allergy Clin. Immunol.* 103:1000.

The invention claimed is:

1. An isolated protein comprising SEQ ID NO:2.

2. A diagnostic kit comprising as reagent the isolated protein according to claim 1.

3. The diagnostic kit according to claim 2 further comprising one or more of known *Phleum pratense* (Phl) allergens selected from the group consisting of Phl p 1, Phl p 2, Phl p 4, Phl p 5a, Phl p 5b, Phl p 6, Phl p 7, Phl p 12 and Phl p 13.

4. An immunoassay comprising the following steps:
(a) obtaining a blood sample from a patient suspected of having a grass pollen allergy;
(b) contacting serum or plasma derived from said blood sample with a reagent comprising the isolated protein according to claim 1 immobilized on a solid phase or in solution; and
(c) detecting the allergy in the patient by detecting IgE antibodies from the serum or plasma bound to the reagent with a detection reagent.

5. The immunoassay according to claim 4 wherein the detection reagent is an enzyme-conjugated anti-IgE antibody.

6. A composition for allergy vaccination of grass pollen allergic patients exhibiting specific binding of IgE antibodies to Phl p 11 comprising a reagent comprising the isolated protein according to claim 1, and optionally a pharmaceutically acceptable carrier.

7. A method for vaccinating patients to prevent an allergic reaction to grass pollen comprising administering to a patient in need thereof the composition according to claim 6.

* * * * *

SEQUENCE LISTING

<160> NUMBER OF SEQ ID NOS: 1

<210> SEQ ID NO 1
<211> LENGTH: 143
<212> TYPE: PRT
<213> ORGANISM: Phleum pratense

<400> SEQUENCE: 1

Asp Lys Gly Pro Gly Phe Val Val Thr Gly Arg Val Tyr Cys Asp Pro
1               5                   10                  15

-continued

```
Cys Arg Ala Gly Phe Glu Thr Asn Val Ser His Asn Val Gln Gly Ala
        20              25              30
Thr Val Ala Val Asp Cys Arg Pro Phe Asn Gly Gly Glu Ser Lys Leu
        35              40              45
Lys Ala Glu Ala Thr Thr Asp Gly Leu Gly Trp Tyr Lys Ile Glu Ile
50              55              60
Asp Gln Asp His Gln Glu Glu Ile Gly Glu Val Val Leu Ala Lys Ser
65              70              75              80
Pro Asp Thr Thr Cys Ser Glu Ile Glu Glu Phe Arg Asp Arg Ala Arg
            85              90              95
Val Pro Leu Thr Ser Asn Asn Gly Ile Lys Gln Gln Gly Ile Arg Tyr
            100             105             110
Ala Asn Pro Ile Ala Phe Phe Arg Lys Glu Pro Leu Lys Glu Cys Gly
        115             120             125
Gly Ile Leu Gln Ala Tyr Asp Leu Arg Asp Ala Pro Glu Thr Pro
    130             135             140
```